United States Patent [19]

Haines et al.

[11] 4,418,944

[45] Dec. 6, 1983

[54] FLUID COUPLING

[76] Inventors: Stephen W. Haines, 13616 Utt Dr., Tustin, Calif. 92680; Stephen R. Marshall, 25971 Cordillera Dr., Mission Viejo, Calif. 92675; Mark E. Steen, 3343 Gingham Ct., Chino Hills, Calif. 91710; Robert C. Swanland, P.O. Box 2815, Riverside, Calif. 92506

[21] Appl. No.: 233,360

[22] Filed: Feb. 11, 1981

[51] Int. Cl.³ .............................................. F16L 35/00
[52] U.S. Cl. ...................................... 285/24; 285/38; 285/156; 285/325; 604/119
[58] Field of Search .................... 285/38, 24, 358, 361, 285/156, 31, 325, 190, 332; 137/315; 251/148, 297, 343, 344, 345; 128/274, 276, 350 R; 604/119

[56] References Cited

U.S. PATENT DOCUMENTS

| Re. 12,688 | 8/1907 | Oakes | 285/150 |
|---|---|---|---|
| 520,988 | 6/1894 | Harrington | 285/150 X |
| 785,130 | 3/1905 | Vanderman | 285/156 X |
| 790,685 | 5/1905 | Hendricks | 285/38 |
| 1,996,218 | 4/1935 | Swanson | 285/325 X |
| 3,395,705 | 8/1968 | Hamilton | 128/276 |
| 4,076,285 | 2/1978 | Martinez | 285/332 |
| 4,258,940 | 3/1981 | Fudge | 285/307 X |

FOREIGN PATENT DOCUMENTS 1009992 11/1965 United Kingdom ................ 285/326
1171097 11/1969 United Kingdom ................ 285/325

Primary Examiner—Dave W. Arola
Attorney, Agent, or Firm—Vorys, Sater, Seymour & Pease

[57] ABSTRACT

A fluid coupling has a male member having a generally rigid base and an attached, relatively resilient face with a first fluid flow path opening from the resilient face. A female member of the coupling has a generally cylindrical receptacle with an opening for admitting the male member and a second fluid flow path for communication with the first fluid flow path in the male member when the male member is inserted into and rotated in the receptacle. The male and female members have cooperating cam surfaces opposite the opening into the fluid flow path in the member for urging the members together with a force directed at the opening. The force compresses the resilient face of the male member against the receptacle to seal the fluid flow paths about the openings. The preferred embodiment is a T coupling in which the male member has a third fluid flow path extending through it and in communication with the first fluid flow path. The third fluid flow path is preferably eccentric of the cross section of the male member to aid and show the rotation of the male member in the receptacle. The male member also preferably has further cam surfaces tapered in the direction of the rotation in the receptacle for aligning the male member in the receptacle.

11 Claims, 7 Drawing Figures

FLUID COUPLING

BACKGROUND OF THE INVENTION

The invention relates to an improved fluid coupling and, more particularly, to an improved T coupling.

Fluid couplings have many uses. One of the more demanding uses is for surgical aspiration. The fluid flow paths including necessary couplings for surgical aspiration must avoid occlusion with tissue fragments and coagulating blood as well as kinking from the required movement of the surgical aspirator. Highly accurate flow rates prohibiting even partial occlusion are also required for aspiration of small body cavities such as the eye. Surgical couplings must also be easily and accurately assembled in an operating theatre and, preferably, sterile. Undesired, equipment damaging leakage flows must also be avoided.

Experience with surgical aspiration devices made by the assignee, Cavitron Corporation, has indicated a need to improve the fluid couplings on the devices and, particularly, a T coupling which provides pressure relief to the aspiration line on command. The pressure relief provides vital control of the extent of aspiration and releases the aspirator without pulling tissue if it attaches to a tissue surface with its suction. The variable height of the aspiration line relative to the aspiration unit as the aspirator is manipulated, however, can cause body liquids to enter the pressure relief line. A check valve was therefore provided in the relief line, but failures of the check valve which was small and delicate to be accommodated in the surgical-sized lines too frequently still allowed liquids into the relief line and damage to the equipment. Flow turbulence and protrusions at the coupling to the relief line also too frequently trapped aspirated tissue particles or coagulated blood, occluding the aspiration line at the coupling to the relief line, and requiring manual manipulation of the coupling to dislodge in a procedure nicknamed "flicking the T". Still further, the coupling arrangement and check valve, although small, held the aspiration line away from the device and thus encouraged aspiration-occluding kinking of the aspiration tube as it curved to the device for the application of the suction. Most importantly, however, the fittings for providing the necessary liquid and air fluid-tight couplings to the pressure relief line which were intended to slip together for easy use actually fit so tightly as to be difficult to use. This encourages operating room personnel to leave the check valve portion of the aspiration line on the aspiration device which, with the resulting accumulation of body salts in reuse, promoted failure of the check valve or, in the alternative, to use plyers in the operating theatre for assembling and disassembling the tubing. Experience with all of these problems clearly pointed to the need for an improved fluid T coupling for introducing the pressure relief fluid flow path to the aspiration fluid flow path.

A relatively new fluid coupling has a generally rigid base portion and an attached, relatively resilient face portion on a male member which is received in a generally cylindrical receptacle of a female member. The receptacle of the female member had an asymmetrical portion adjacent an opening into the receptacle so that the male member could be inserted and urged with a camming action upon rotation to compress the resilient face portion of the male member into fluid tight, sealing engagement with the receptacle with the least rotation of the male member in the receptacle. Fluid flow paths opening from the receptacle of the female member and the face portion of the male member were thus brought into sealed communication with a force diagonal of their junction. This fluid coupling therefore had promise for surgical use in providing a fluid coupling of just two, easily assembled components, but had not been used before for the more exacting requirements of a T coupling having both a through-flow path and a communicating, coupled path for both liquid and gas fluid communication as required for surgical aspiration pressure relief. An improved, T coupling embodiment was therefore required.

SUMMARY OF THE INVENTION

It is therefore an object of the invention to provide an improved fluid coupling of the type having a male member with a rigid base portion and an attached, relatively resilient face portion and, more particularly, an improved fluid T coupling for, for example, surgical aspiration use.

To this end, the invention provides unique features to a fluid coupling of the type having a male member with a generally rigid base portion and an attached, relatively resilient face portion which is received in an open sided, generally cylindrical receptacle of a female member. To provide tighter sealing compression at openings to fluid flow paths in the receptacle of the female member and the resilient face portion of the male member, one of the male and female members is provided with a projecting cam surface in a position opposite the opening to the fluid flow path in the member for engaging a cooperating surface on the other member for urging the members together with a force directed at the opening. Having the camming surfaces opposite the fluid path opening also makes it possible to avoid compressing the male face against the female receptacle and consequent friction resistance to rotation for aligning the flow path openings until alignment is imminent for easier use.

In a preferred, T coupling embodiment, a fluid flow path through the male member communicates with the beforementioned flow path of the male member. It is preferably eccentric of the cross section of the male member in the female receptacle. This provides two advantages. First, as the male member is rotated in the receptacle to engage the cam surface for sealing the openings to the fluid flow paths communicating between the male and female members, the connections to the through flow path are moved arcuately rather than axially twisted to minimize the rotational forces which could cause the connections to the through flow path to disconnect. Second, the arcuate movement of the through flow path is more readily apparent than axial rotation to provide visual and tactile confirmation of the rotational movement providing the seal.

A second cam surface on one of the male and female members of the preferred embodiment is tapered in the direction of the rotation for aligning the openings to the fluid flow paths. A handle preferably projects from the male member for rotating it.

DESCRIPTION OF THE DRAWINGS

These and still other features of the invention will now be described with reference to drawings of a preferred embodiment which is intended to illustrate but not to limit the invention and in which.

DESCRIPTION OF THE PREFERRED EMBODIMENT

Figure 2:
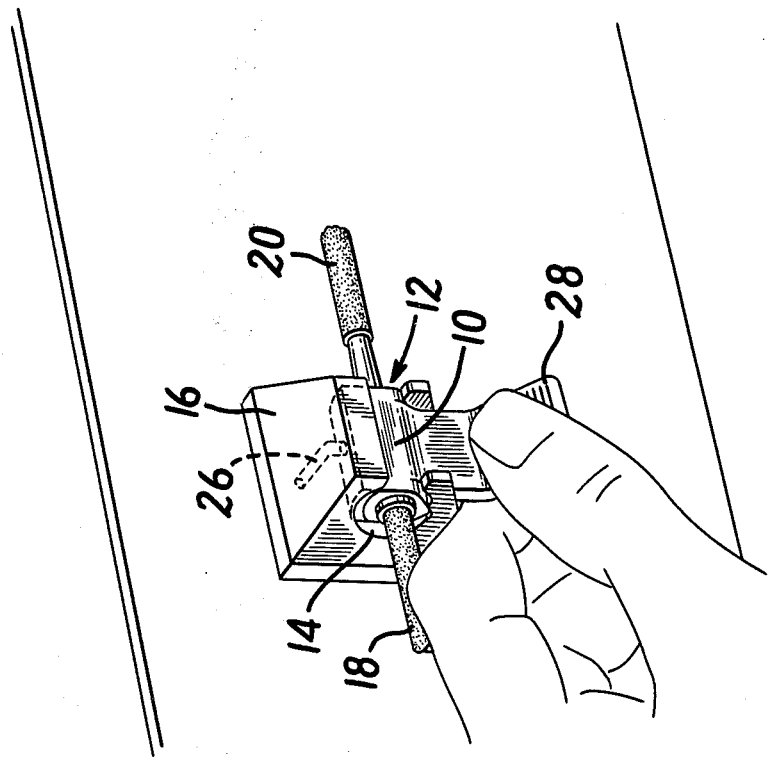
FIG. 2 is a perspective view of the preferred embodiment in a final position.
Figure 1:
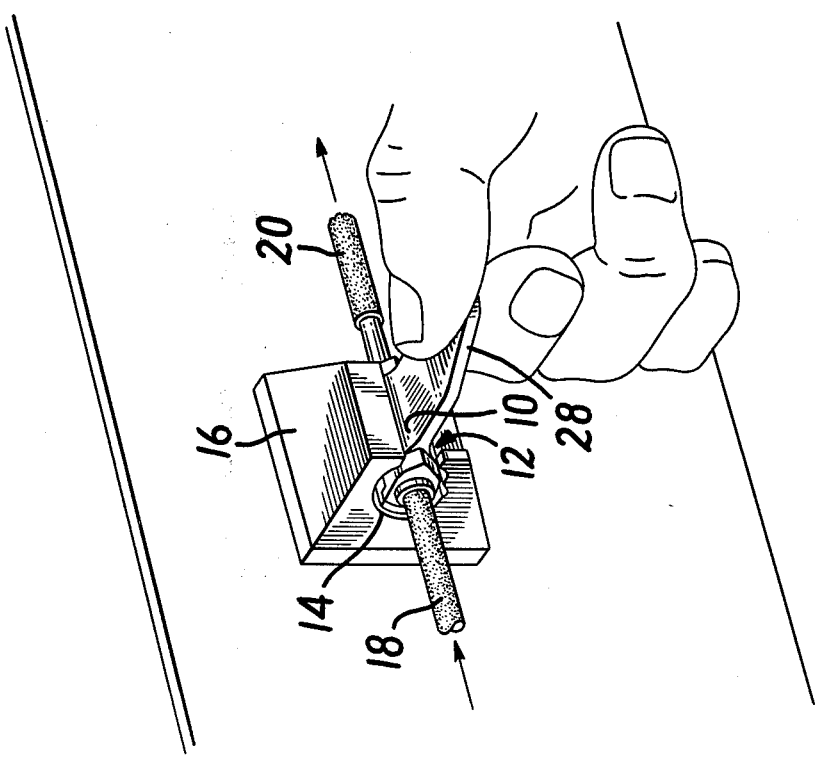
FIG. 1 is a perspective view of the preferred embodiment in an initial position.

FIG. 1 shows the male member 10 of the preferred embodiment as it is initially inserted into a slot at 12 in a surface 13 leading to a generally cylindrical receptacle 14 of a female body member 16. Tubes 18, 20 connect to opposite ends of a (third) fluid flow path 22 (FIG. 5) through the male member from opposite ends at the open ends of the cylindrical receptacle of the female member. When the male member is inserted into the receptacle 14 and rotated in the receptacle as shown in FIG. 2, an opening 24 (FIG. 5) into a first fluid flow path 25 in the male member which communicates with the through flow path 22 aligns with an opening 32 to a fluid flow path 26 extending from the receptacle of the female member. The coupling therefore is a T coupling.

The T coupling is intended for use on a surgical aspirator (not shown) in which body liquids and tissue fragments are drawn through tube 18 and through-flow path 22 by suction applied to tube 20. The fluid flow path 26 in the female member is connected to a pair of check valves (not shown) in the device which prevent the body liquids in the aspiration line 18, 20, 22 from entering the aspiration device, but allow gas fluid (air) to enter the aspiration path 22 (FIG. 5) to relieve the suction in the aspiration tube 18 when desired. The aspiration tubes 18 and 20 and male member 10 are provided as a sterile unit for disposable use with each surgical operation. A handle 28 on the male member makes it easy to insert the male member into the female receptacle and rotate it to align and seal the flow paths as later described, and then remove the aspiration tubes and male member at the end of use. A sterile T coupling which is easy to use in a surgical environment is therefore provided.

Figure 4:
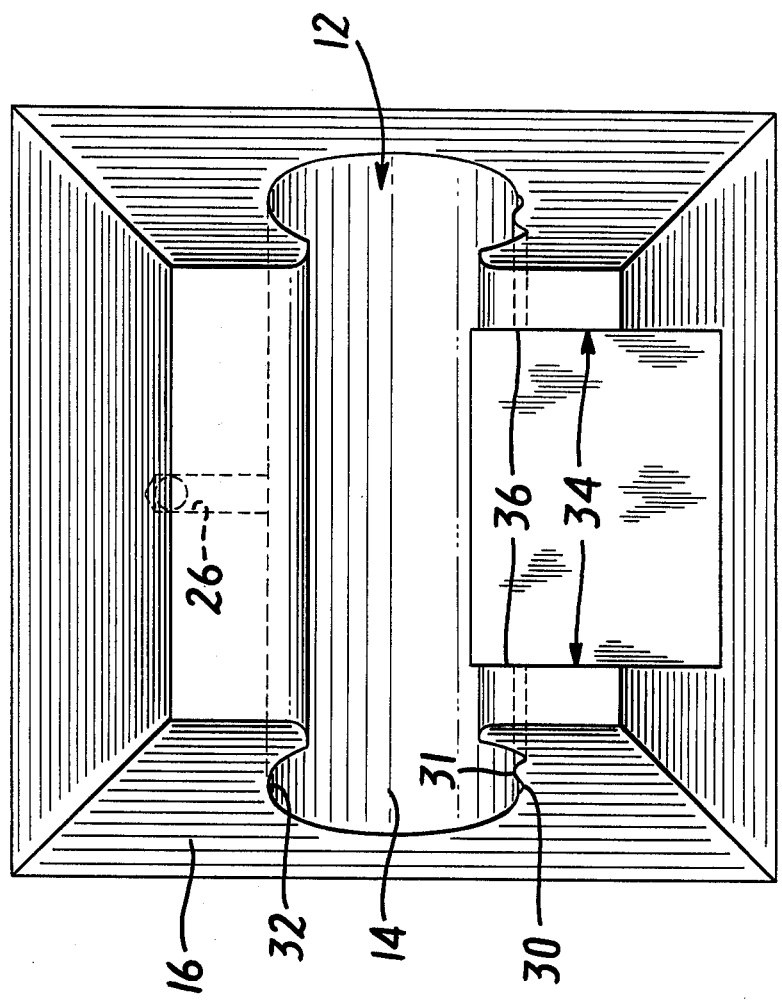
FIG. 4 is a front view of the female member.
Figure 3:
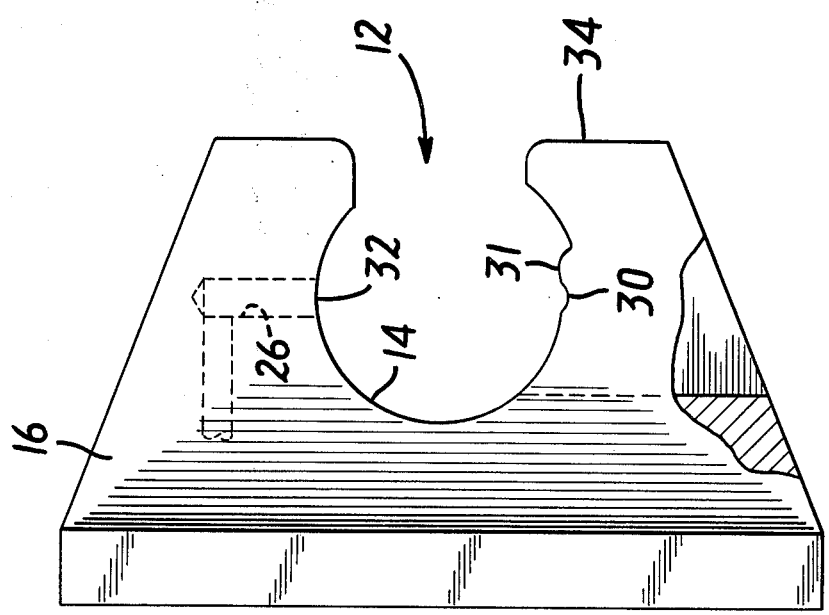
FIG. 3 is a side view of a female member of the preferred embodiment.
Figure 7:
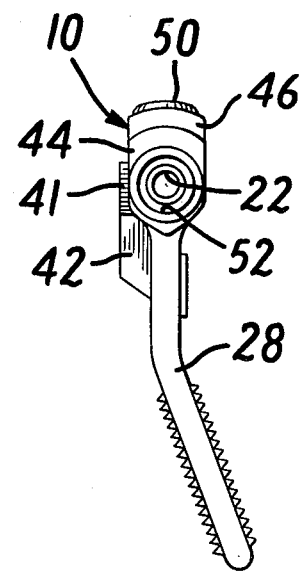
FIG. 7 is a side view of the male member.

FIGS. 3 and 4 show the female member 16 in greater detail. A configured surface 30, 31 is positioned on the generally cylindrical wall of the receptacle 14 on the side portion substantially diametrically opposite the opening 32 into the fluid flow path 26 in the female member. The configured surface portion cooperates with a cam surface 33 (FIG. 7) on the male member to urge the male member toward the opening 32 when the male member is inserted into the receptacle and rotated to align the opening 24 (FIG. 5) of its fluid flow path with the opening 32 to the fluid flow path in the female member. Having the force urging the male and female members together in line with the openings to the fluid flow paths in this way provides the most desireable sealing force. As shown in FIG. 7, the male member has two generally flattened sides to enable it to be passed, when oriented in one position, through the opening 12 and to be retained in the generally cylindrical receptacle 14 when rotated from this first position.

The configured surface on the receptacle includes a detent 30 which receives the cam surface 33 of the male member when the fluid flow path openings 24, 26 in the male and female members are aligned, and a raised or cam portion 31 adjacent the detent on the side toward the opening 12 into the receptacle. The remaining portion of the receptacle from the raised portion 31 to the opening 12 is dimensioned from the opposite wall of the receptacle to freely admit the male member including its cam surface 33.

The female member also has a space at 34 for receiving the handle 28 of the male member when the male member is rotated in the female receptacle to align the fluid flow path openings 24, 32. This forms a pair of arms 36 at opposite end portion of the bottom of the otherwise generally cylindrical receptacle. It should be understood, however, that other embodiments may have only a single, central arm projecting through an opening in the handle of the male member or substantially broader or continuous arms if the handle were narrower or omitted. The facing sides of the arms 36 cooperate as camming surfaces with a pair of tapered further cams 41 (FIG. 6) on the male member to aid in aligning the male member longitudinally of the cylindrical receptacle or axially of the rotation for aligning the fluid flow paths in the male and female members. The back surfaces 37 of the female member between the arms 36 engages stop projections 42 on the male member which are the body part of the cams 41 to rotationally align the fluid flow path openings 24, 32. It should also be understood that the configured wall portion including the detent 30 and cam 31 may extend along substantially the full length of the generally cylindrical wall of the receptacle or only a portion thereof. Thus, in the drawings, the configured portion is located only adjacent the end portions of the receptacle in the portion of the cylindrical wall defined by the arms 36.

Figure 5:
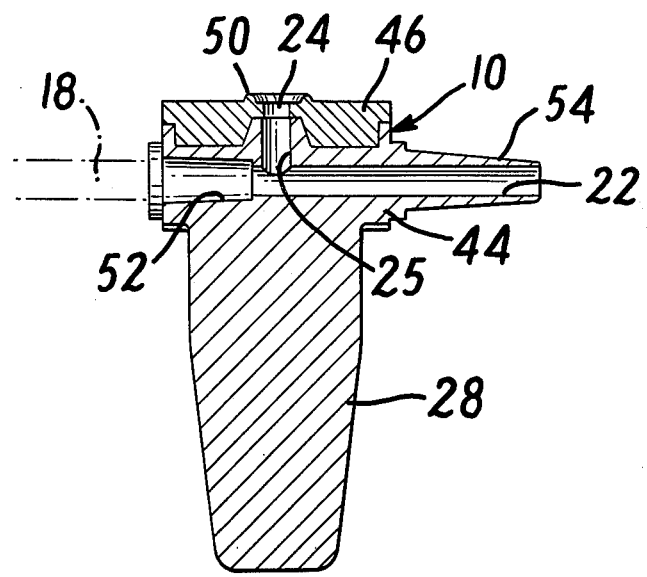
FIG. 5 is a front, setional view of a male member of the preferred embodiment.
Figure 6:
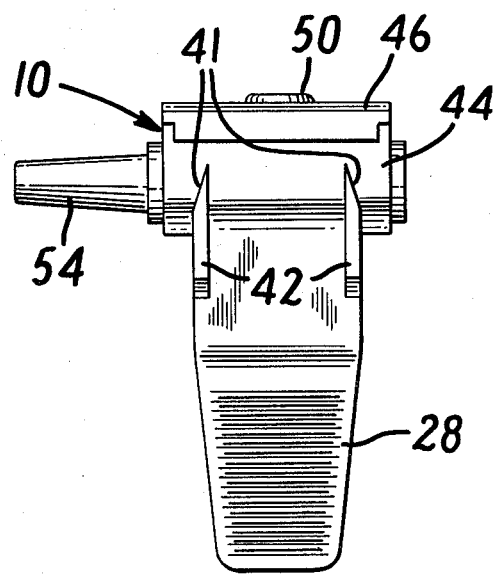
FIG. 6 is a back view of the male member.

FIGS. 5, 6 and 7 show the male member of the coupling. As shown in FIG. 5, the male member has a body portion 44 which is generally rigid and an attached face portion 46 which is relatively resilient. The face and body portions of the male member are preferably molded together as a unit with suitably resilient and rigid plastics such as medical grade PVS and medical grade ABS. The opening 24 to the first fluid flow path 25 in the male member is in the resilient face portion of the male member so that the force provided by the opposite cam 33 on the male member against the surface 30 of the female member compresses and seals the face portion about the opening 24 to the receptacle of the female member. A ridge 50 surrounds the opening 24 to further aid in the sealing, like a washer.

The third fluid flow path 22 through the male member is shown in FIG. 5 to have an enlarged end 52 for receiving the aspiration tube 18 and providing a substantially continuous internal diameter between the tube 18 and the fluid flow path 22. This encourages laminar flow of the fluid from the tube 18 through the male member and eliminates any projections which could catch tissue particles and coagulating blood. Both features contribute to minimizing occlusion of the fluid flow path 22. The other end of the fluid flow path 22 has a nipple 54 which provides a similar smooth flow path into the tube 20 (FIG. 1) which provides the suction for aspiration. The fluid flow path 22 is also seen to be eccentric of the cross section of the male member from the face 46 to the cam 33. This minimizes twisting of the connections to the tubes 18, 20 when the male member is rotated in the receptacle to align the openings 24, 32 which could twist off the tubes, and also provides an arcuate movement which more clearly shows the rotation.

FIGS. 6 and 7 further show the eccentric position of the fluid flow path 22. They also show tapered projections 41 on the male member which provide the camming action with the arms 36 of the female member for aligning the male member longitudinally of the receptacle and the fluid flow path openings 24, 32 with each other as the male member is rotated in the receptacle until the body or stop part 42 of the cams engages the back 37 of the female member.

OPERATION

The male member 10 is first inserted into the slot 12 of the female member 14 with the cam 33 at the slot. It is then rotated with handle 28 to slide the cam 33 freely to the raised portion 31 of the configured surface of the receptacle, the tapered cams 41 on the male member engaging the facing camming surface sides of arms 36 on the female member to align the members longitudinally. The cam 33 then rides up the rise 31, compressing the resiliant face portion 46 of the male member, preferrably about 0.025 in., and providing with the consequent resistance to rotation tactile indication of impending mating. With slight further rotation, the cam 33 drops into the detent 30, partly releasing the face compression, preferably to about 0.020 in., and tactily indicating mated, compression-sealed alignment of the openings 24, 32 into the fluid flow paths 25, 26 of the male and female members. At the same time, the stop portions 42 of the male member butt the back 37 of the female member to prevent further rotation. The position of the cam 33 opposite the opening 24 to the fluid flow path in the male member desirably directs the compression sealing force to the opening.

We claim:

1. In a fluid coupling having a male member including a generally rigid base portion and an attached, relatively resilient face portion and a first fluid flow path, having a centerline, extending therethrough from an opening in the resilient face portion, and a female member including a body portion having a generally cylindrical bore extending therethrough with an opening in one wall of the female body portion communicating with the bore along its full length and cooperating therewith to form a generally C-shaped receptacle for receiving and rotatably supporting the male member, the female member having a second fluid flow path opening from a generally arcuate wall of the receptacle for fluid communication with the first fluid flow path in the male member, the improvement comprising, first cam surface means formed on said female member in substantially diametrically opposed relation to said second fluid flow path opening, second cam means on said male member in position to engage and cooperate with said first cam means on said female member, said second cam means being located on said male member on a surface thereof substantially opposite said first fluid flow path opening, said male member being dimensioned when oriented in a first position to be passed through said opening in said one wall of the female member into said receptacle, and to be retained in the receptacle when rotated to a second position, said first fluid flow path opening and said second fluid flow path opening being aligned and in fluid communication when said male member is in said second position, detent means on one of said male and female members and cooperating with the other of said male and female members to releasably retain said male member in said second position, means for aligning said first fluid flow path and said second fluid flow path in said second position, said first and said second cam means being located to urge said male and female members together whereby said resiliently face portion is forced into sealing engagement with said female member with a sealing force directed along the opening to the fluid flow path in the male member when the male member is rotated to the second position, and a substantially linear third fluid flow path having a centerline and extending through the male member from end portions received at ends of the receptacle and transversely to and in communication with the first fluid flow path, said first fluid flow path and said third fluid flow path being oriented such that the centerlines of said first fluid flow path and said second fluid flow path essentially intersect, whereby the fluid coupling is a T coupling, said rotation being about an axis substantially parallel to said linear third fluid flow path.

2. A fluid coupling as in claim 1, wherein the third fluid flow path is eccentric of the cross section of the male member in the receptacle.

3. A fluid coupling as in claim 1, wherein an end of the third fluid flow path is enlarged for receiving a tube and providing a substantially uniform internal cross section between the tube and third fluid flow path.

4. A fluid coupling as in claim 3, wherein the other end of the third fluid flow path is a nipple for projecting into another tube.

5. A fluid coupling as in claims 1, 2, 3 or 4; and further comprising a handle extending from the male member opposite the first fluid flow path opening.

6. A fluid coupling as in claims 1, 2, 3 or 5; wherein said means for aligning said first fluid flow path and said second fluid flow path comprises at least one third cam surface on one of the male and female members which is tapered in the direction of rotation of the male member in the receptacle of the female member to move the fluid flow path openings toward communication with each other and cooperative with the camming surfaces on the other member for positioning the members relative to each other with the rotation for aligning the openings with each other in the direction of the axis of the rotation.

7. A fluid coupling as in claim 6 wherein said means for aligning said first fluid flow path and said second fluid flow path comprises comprising a stop body portion on the third cam surface for butting the other member to stop further rotation.

8. A male member adapted to cooperate with a female member of a fluid T coupling, the female member having cam means, alignment means and a generally cylindrical receptacle for receiving the male member and a fluid flow path opening therefrom, the male member comprising:

an elongated base portion adapted to be rotatably supported in the generally cylindrical receptacle;

a face portion which is resilient relative to the base portion attached to the base portion and having a first fluid flow path opening therefrom for communication with the fluid flow path opening in the receptacle of the female member, said first fluid flow path having a centerline;

a second substantially linear fluid flow path, having a centerline, extending longitudinally through the male member generally transverse to and in communication with the first fluid flow path in the male member, the centerline of said first fluid flow path and the centerline of said second fluid flow path essentially intersecting, cam means adapted to cooperate with said cam means on the female member for compressing the resilient face portion into sealing engagement with the female member at the fluid flow path openings when the male member is rotated in the receptacle portion of the female member, said cam means on said male member including a cam lobe projecting from the male member opposite to the opening of the first fluid flow path therein, and alignment means adapted to cooperate with said alignment means on the female member for aligning the fluid flow openings in the male member and the female member when the male member is rotated in the receptical portion of the female member.

9. A male member as in claim 8; wherein the ends of the receptacle of the female member are open; and wherein the other fluid flow path in the male member extends between ends thereof at the open ends of the receptacle and is eccentric of the cross section of the male member in the receptacle.

10. A male member as in claim 8 or 9, wherein said alignment means comprises a second cam surface on the male member tapered in the direction of the rotation of the male member in the receptacle and cooperative with camming surfaces on the female member for positioning the members relative to each other with the rotation to align the fluid flow path openings with each other in the direction of the axis of rotation.

11. A male member as in claim 10; wherein said alignment means comprises a stop body portion on the second cam surface for butting the other member to stop further rotation.

* * * * *